(12) United States Patent
Oida (10) Patent No.: US 8,749,789 B2
(45) Date of Patent: Jun. 10, 2014

(54) GAS CONCENTRATION MEASURING APPARATUS

(75) Inventor: Takuji Oida, Kyoto (JP)

(73) Assignee: Horiba, Ltd., Kyoto (JP)

(*) Notice: Subject to any disclaimer, the term of this patent is extended or adjusted under 35 U.S.C. 154(b) by 12 days.

(21) Appl. No.: 13/330,927

(22) Filed: Dec. 20, 2011

(65) Prior Publication Data

US 2012/0162655 A1 Jun. 28, 2012

(30) Foreign Application Priority Data

Dec. 27, 2010 (JP) .................................. 2010-290924

(51) Int. Cl.
*G01N 21/00* (2006.01)

(52) U.S. Cl.
USPC ......................................... 356/437; 356/438

(58) Field of Classification Search
USPC .................................................. 356/432–444
See application file for complete search history.

(56) References Cited

U.S. PATENT DOCUMENTS

| 5,457,320 | A | * | 10/1995 | Eckles et al. | 250/345 |
| 5,464,983 | A | * | 11/1995 | Wang | 250/343 |
| 7,936,460 | B2 | * | 5/2011 | Iwase et al. | 356/438 |

FOREIGN PATENT DOCUMENTS

| JP | 58-160849 A | 9/1983 |
| JP | 64-2889 B2 | 1/1989 |
| JP | 2010-000010 A | 1/2010 |
| JP | 2010-000010 A | 1/2010 |

* cited by examiner

*Primary Examiner* — Tri T Ton
(74) *Attorney, Agent, or Firm* — Global IP Counselors, LLP (57) ABSTRACT

A gas concentration measuring apparatus for measuring a concentration of a measurement target substance contained in a sample gas includes a light source unit in which a light source is arranged, and a sensor unit that is arranged on an optical path of the light source. The sensor unit includes a concentration measuring sensor configured to receive light from the light source after the light has passed through a sample cell unit and measure a concentration of the measurement target substance. The apparatus further includes an introducing device configured to introduce the sample gas to a vicinity of concentration measuring sensor. Therefore, a vicinity of the concentration measuring sensor is filled with an atmosphere of the sample gas so that a concentration of a measurement target substance contained in the sample gas is measured stably and accurately regardless of fluctuations in an ambient atmosphere of a measuring environment.

17 Claims, 11 Drawing Sheets

GAS CONCENTRATION MEASURING APPARATUS

CROSS-REFERENCE TO RELATED APPLICATIONS

This U.S. National stage application claims priority under 35 U.S.C. §119(a) to Japanese Patent Application No. 2010-290924, filed in Japan on Dec. 27, 2010, the entire contents of Japanese Patent Application No. 2010-290924 are hereby incorporated herein by reference.

BACKGROUND

1. Field of the Invention

The present invention relates to a gas concentration measuring apparatus.

2. Description of the Related Art

Apparatuses exist that are configured to measure concentrations of various gasses. For example, when refined air (medical air) is prepared onsite at a medical facility, the medical air can be prepared using an apparatus that mixes 100% $O_2$ gas from a gas cylinder with 100% $N_2$ gas from a gas cylinder at a prescribed ratio. Alternatively, the medical air can be prepared using an air refining apparatus that is capable of performing compressing, drying, and dust processing functions. In either of these apparatuses, the concentration of carbon dioxide ($CO_2$) in the prepared medical air is measured continuously and controlled so that the amount of $CO_2$ does not exceed a prescribed maximum of, for example, 500 ml/m$^3$ (500 ppm).

A $CO_2$ analyzer can also be provided in an apparatus, such as a photosynthesis evaluation apparatus, for evaluating a $CO_2$ absorption or $CO_2$ emission function of a plant. The evaluation apparatus can be, for example, an apparatus such as that disclosed in Laid-open Japanese Patent Application 2010-10. That is, the evaluation apparatus can be configured to evaluate a $CO_2$ absorption function or a $CO_2$ emission function of a plant during photosynthesis in a natural environment. A $CO_2$ analyzer can be provided among the components of the evaluation apparatus for measuring a $CO_2$ concentration to determine the $CO_2$ absorption function or the $CO_2$ emission function of the plant with a high degree of measurement accuracy.

Figure 10:
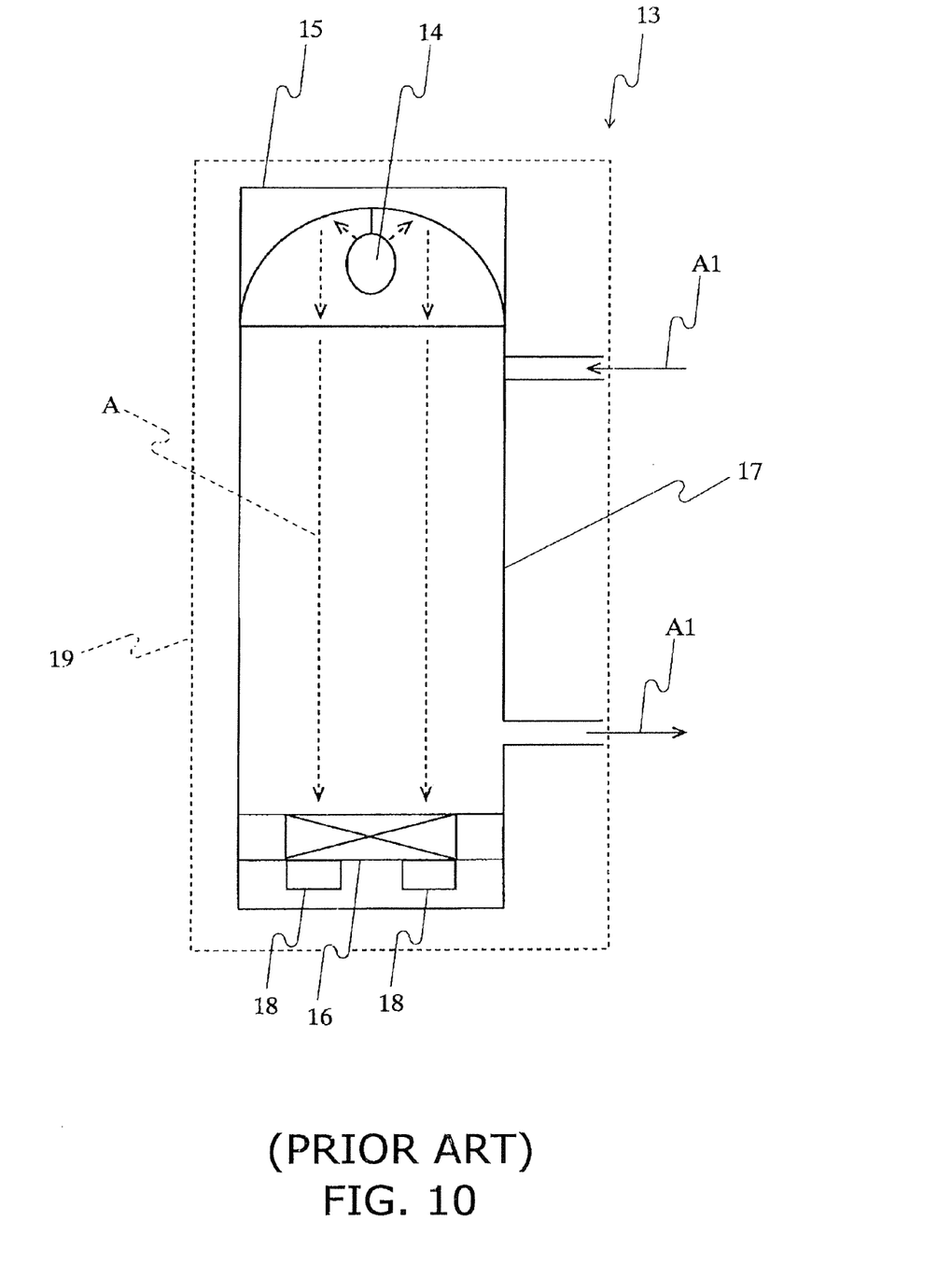
FIG. 10 is a schematic view for explaining a conventional gas concentration measuring apparatus.
Figure 11:
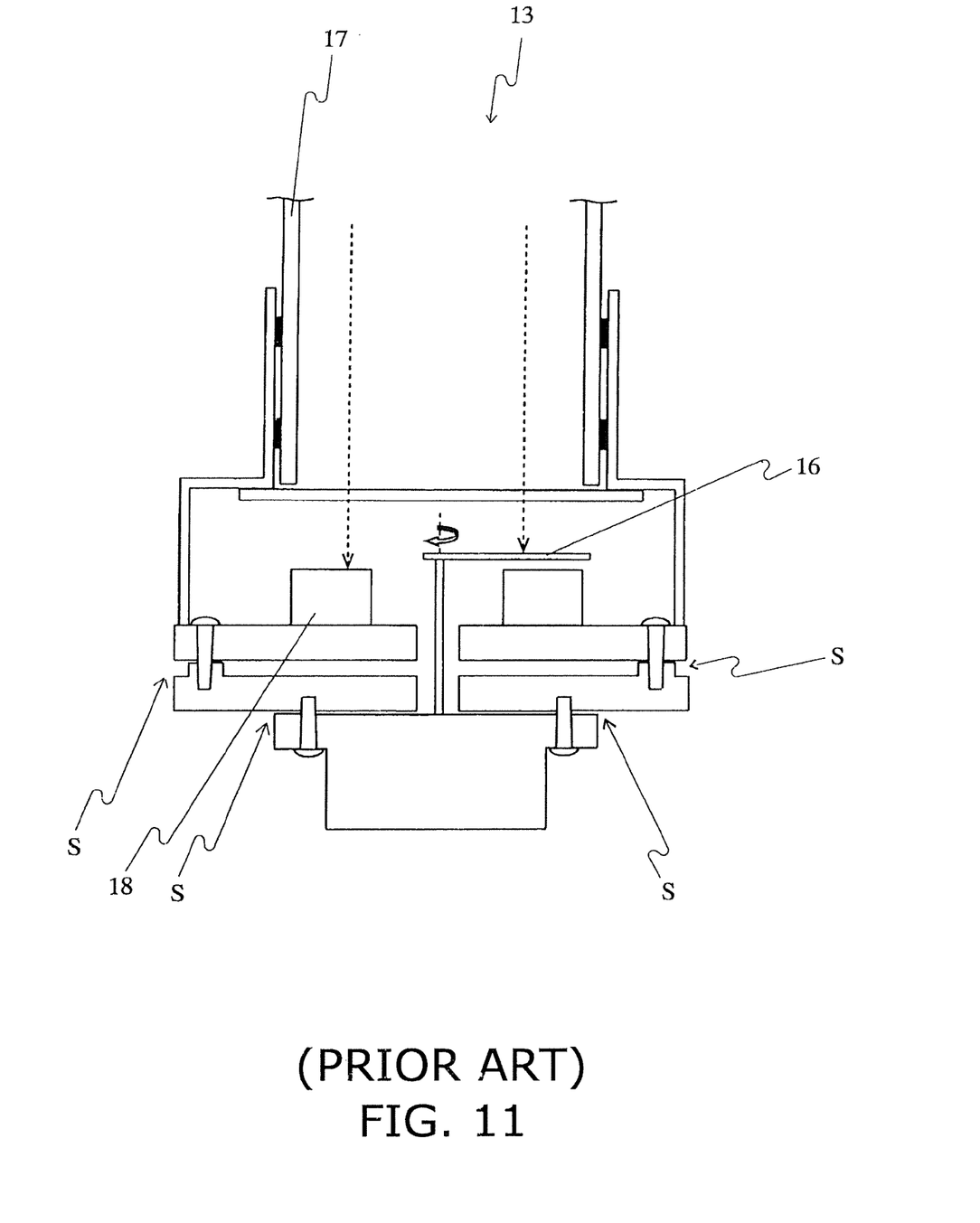
FIG. 11 is an enlarged schematic view showing features of the conventional gas concentration measuring apparatus.

In such an apparatus, a sample gas can be measured by measuring a $CO_2$ concentration using a non-dispersive infrared absorption technique that can be performed by an apparatus as shown, for example, in FIGS. 10 and 11. That is, the gas concentration measuring apparatus 13 includes a light source unit 15 in which a light source 14 is arranged, a light shuttering device 16 that is configured to block or pass light as necessary, a sample cell unit 17 in which a sample cell is arranged, and a concentration measuring sensor 18 (detection device).

In order to measure $CO_2$ and other components contained in atmospheric air in minute amounts, a highly sensitive measurement is typically necessary because the contents of such components are on the order of only several hundred parts per million. Therefore, a Kanthal wire or other filament that emits a large amount of light is used as the light source 14, and a chopper or other light shuttering device 16 is provided to block the light intermittently as necessary. If a chopper is used, a motor and an external electric power source are provided to drive the chopper. Thus, the number of parts of the gas concentration measuring apparatus 13 will be increased. As a result, it will be easier for a gap S to form between the sample cell and the concentration measuring sensor 18.

Also, while the concentration of $CO_2$ in atmospheric air is generally approximately 300 to 400 ppm, the concentration of $CO_2$ in a person's breath is several percent. Consequently, if the gas concentration measuring apparatus 13 is installed in a place where people come and go and/or the gas concentration measuring apparatus 13 is operated by a person, then the concentration of $CO_2$ surrounding the gas concentration measuring apparatus 13 will typically fluctuate. Similarly, if a combustion apparatus is installed near the gas concentration measuring apparatus 13, then the concentration of $CO_2$ surrounding the gas concentration measuring apparatus 13 will rise and the concentration of $CO_2$ surrounding the optical system (in particular, the concentration measuring sensor 18) will fluctuate, thus making it difficult to measure the $CO_2$ concentration accurately.

Additionally, even if the apparatus is installed in a location where access by people is restricted, a standard concentration of $CO_2$ for the inside of designated buildings (e.g., commercial facilities and offices) is stipulated to be 1000 ppm or less according to typical building management laws. However, this concentration is higher than the standard for medical air. Consequently, even if the gas concentration measuring apparatus 13 is installed in a place where access restricted, there is a possibility that the concentration of a targeted measurement substance cannot be measured with sufficient stability or accuracy. In an attempt to avoid these issues, the entire gas concentration measuring apparatus 13 can be enclosed in an apparatus housing case 19 as shown in FIG. 10. The apparatus housing case 19 is completely sealed to prevent ambient air from flowing into the gas concentration measuring apparatus 13. For example, all gaps are filled with a sealing material, and each gap of the analyzer is purged with $N_2$ or another inert gas, such as that described in Japanese Examined Patent Publication No. S64-002889.

Furthermore, the problems discussed above are not limited to measuring the concentration of $CO_2$ in medical air, but also occur when measuring the concentration of $H_2O$ in air. The same or similar problems also exist when measuring a $CO_2$ concentration in order to understand a $CO_2$ absorption or emission function of a plant using the aforementioned photosynthesis evaluating apparatus.

SUMMARY

When the entire apparatus will be enclosed in a completely sealed case as discussed above, the size of the apparatus is increased. Also, when the apparatus will be operated by a person, the apparatus is configured to be operated from the outside, which is difficult to achieve technically and from cost perspective. Furthermore, even if the gaps are filled with a sealing material, it is difficult to seal all gaps so that no leaks occur. In addition, the sealing material will need to be removed and replaced when maintenance is performed on the apparatus. Thus, even if sealing can be accomplished, the sealing can result in additional work and cost.

With the gas concentration measuring apparatus described in Japanese Examined Patent Publication No. S64-002889, the apparatus tends to be insusceptible to fluctuations in the ambient atmosphere of the measuring environment, such as increased measurement values caused by detecting the higher concentration of $CO_2$ contained in a person's breath, because the gaps in the optical system are purged with an inert gas. However, the apparatus can be problematic from a cost perspective because it is necessary to constantly supply an inert gas other than the target substance being measured to serve as the purge gas. It is also necessary to provide equipment for introducing the inert gas.

Therefore, an object of the present invention is to provide a gas concentration measuring apparatus that can stably and accurately measure a concentration of a measurement target substance contained in a sample gas by filling a vicinity of a concentration measurement sensor with the sample gas so that the measurements are not affected by fluctuations of an ambient measurement environment.

Examples of embodiments for achieving the aforementioned object will now be explained. These embodiments can be combined in any combination as necessary.

One disclosed embodiment provides a gas concentration measuring apparatus configured to measure a concentration of a measurement target substance contained in a sample gas. The apparatus includes a light source unit having a light source, and a sample cell unit that is arranged on an optical path of the light source and configured so that a sample gas can be introduced into the sample cell. The apparatus further includes a sensor unit that is arranged on an optical path of the light source and has a concentration measuring sensor that is configured to receive light from the light source after the light has passed through the sample cell unit and measure a concentration of a measurement target substance. In addition, the apparatus includes an introducing device that is configured to supply the sample gas to a vicinity of the sensor unit or the light source unit and fill an inside of the sensor unit or the light source unit with an atmosphere of the sample gas.

With a gas concentration measuring apparatus according to this embodiment, since a vicinity of the concentration measuring sensor or the light source is filled with an atmosphere of the sample gas, a concentration of the measurement target substance in the sample gas can be measured stably and accurately even if an ambient atmosphere of a measuring environment fluctuates. Also, the cost of the gas concentration measuring apparatus can be reduced because it is not necessary to prepare a separate purge gas, it is not necessary to protect the apparatus with a sealed case, and it is not necessary for the apparatus to be configured so that the gaps in the apparatus are drastically reduced.

The gas concentration measuring apparatus can further include a light shuttering mechanism that is arranged near the concentration measuring sensor or the light source and configured to intermittently block infrared light emitted from the light source. Therefore, instead of intermittently shining infrared light from the light source, the infrared light is shone continuously while the optical path of the infrared light is intermittently blocked. Consequently, it is possible to artificially treat the infrared light reaching the concentration measuring sensor as intermittently emitted light.

In addition, the light shuttering mechanism can include a chopper. Furthermore, an introducing device can be provided near the light shuttering mechanism. Therefore, since a vicinity of the light shuttering mechanism is filled with an atmosphere of the sample gas, a concentration of the measurement target substance in the sample gas can be measured stably and accurately even if an ambient atmosphere of a measuring environment fluctuates. More particularly, it is easy for gaps to occur between the sample cell and the concentration measuring sensor or the light source since an external electric power source and a motor to drive the light shuttering mechanism causes the total number of parts to increase. By providing the introducing device near the light shuttering device, the problems associated with providing the light shuttering device in the gas concentration measuring apparatus can be resolved.

Furthermore, the introducing device can include a cover that covers a connection portion between the sample cell unit and the sensor unit or the light source unit. The sample gas can be introduced to the cover. Therefore, since an inside of the cover can be filled with the sample gas, fluctuations of the sample gas atmosphere surrounding the concentration measuring sensor can be prevented. As a result, a concentration of the measurement target substance contained in the sample gas can be measured more stably and accurately.

Furthermore it is acceptable for the introducing device to have a cover member that covers the entire sensor unit or light source. Thus, the sample gas can be introduced to the cover. Accordingly, since an inside of the cover member can be filled with the sample gas, fluctuations of the sample gas atmosphere surrounding the concentration measuring sensor can be prevented. As a result, a concentration of the measurement target substance contained in the sample gas can be measured more stably and accurately.

It is also acceptable for the introducing device to further include a scrubber arranged in a gas flow passage.

With this arrangement, if the sample gas is, for example, an exhaust gas or other gas containing particulates, harmful particles and/or components can be adsorbed and removed such that a more accurate measurement can be accomplished. Additionally, damages to the apparatus can be prevented.

It is also acceptable for the introducing device to be provided between the sample cell unit and the sensor unit or the light source unit and to have a partitioning wall in which communication holes are formed.

It is further acceptable for the measurement target substance contained in the sample gas to be $CO_2$ or $H_2O$. Thus, the ability of these measurement target substances to absorb infrared light can be utilized to achieve an accurate measurement by, for example, using a non-dispersive infrared absorption method to compare the target substances with respect to an inert gas.

The disclosed embodiments thus provide a gas concentration measuring apparatus that fills a vicinity of a concentration measurement sensor with the sample gas to stably and accurately measure a concentration of a measurement target substance contained in a sample gas without being affected by fluctuations of an ambient measurement environment.

DETAILED DESCRIPTION OF EMBODIMENTS

Figure 1:
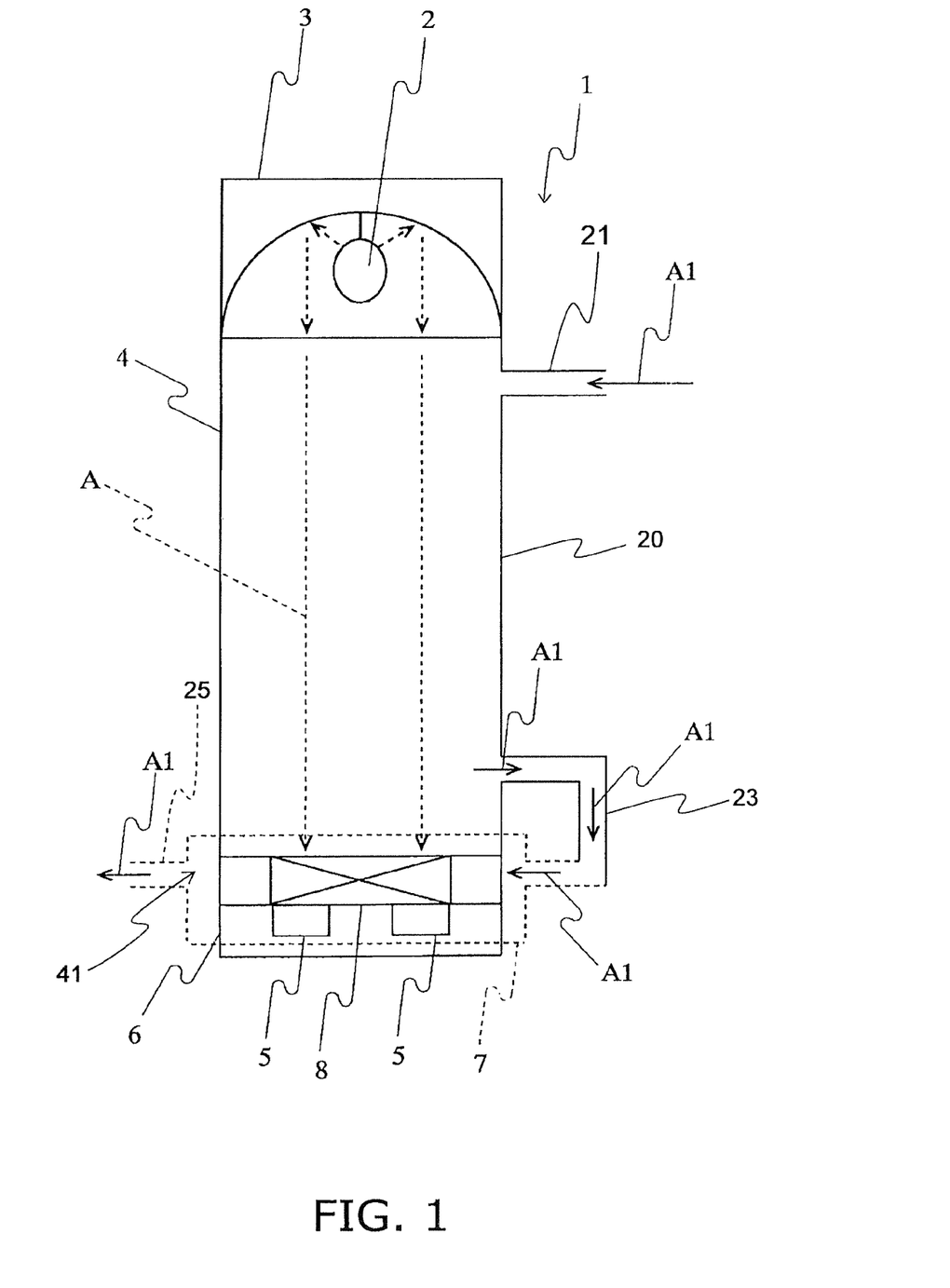
FIG. 1 is a schematic view for explaining a gas concentration measuring apparatus according to an exemplary embodiment.
Figure 2:
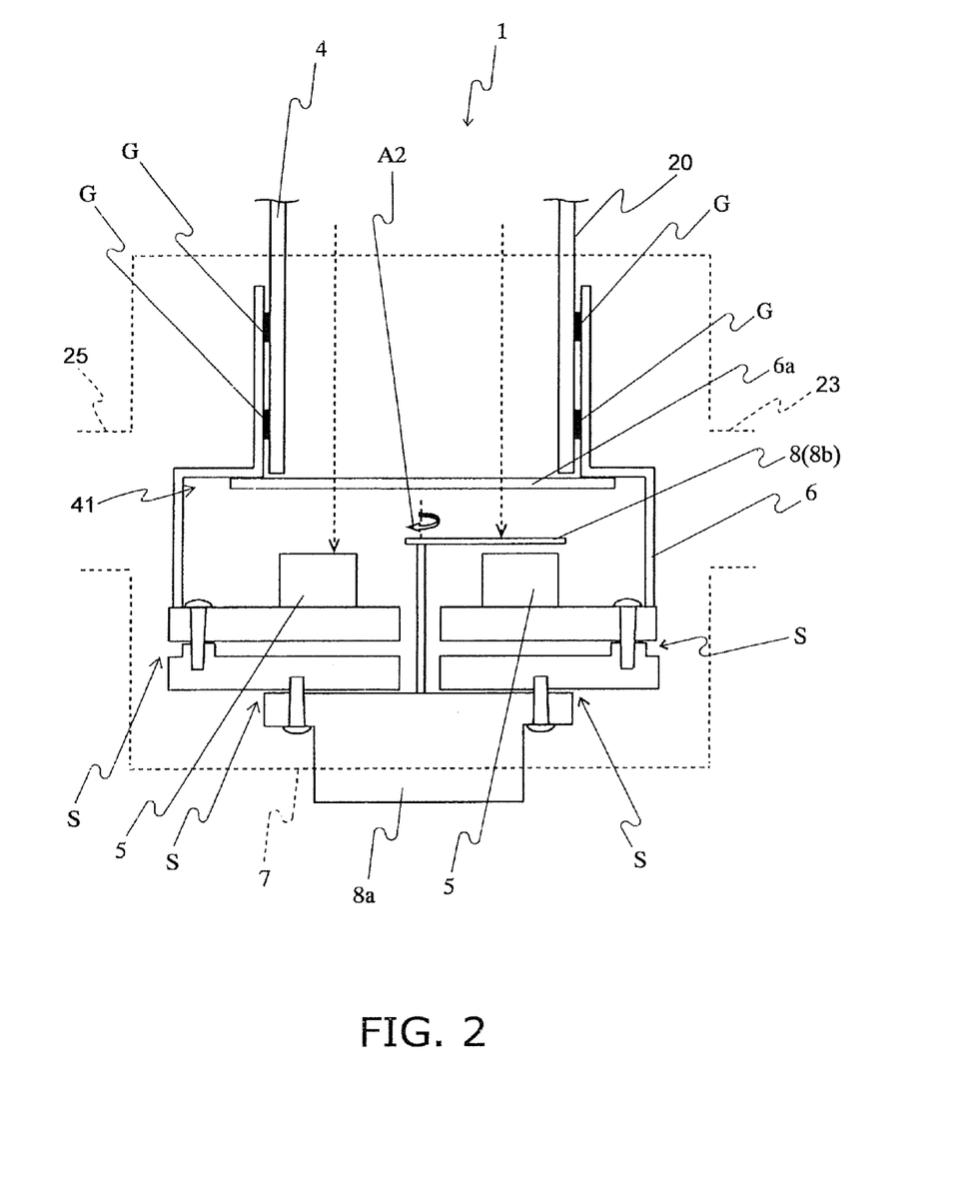
FIG. 2 is an enlarged schematic view showing additional features of the gas concentration measuring apparatus shown in FIG. 1.

As shown in FIGS. 1 and 2, a gas concentration measuring apparatus 1 according to an exemplary embodiment comprises a light source unit 3 in which a light source 2 is arranged, a sample cell unit 4 that is arranged on an optical path of the light source 2 and an introducing device as discussed herein that is configured to introduce a sample gas into the sample cell unit 4. A sensor unit 6 is arranged on an optical path of the light source 2 and has a concentration measuring sensor 5 that is configured to receive light from the light source 2 after the light has passed through the sample cell unit 4 and measure a concentration of a measurement target substance.

It should be noted that there are no particular limitations on the light source 2 of the light source unit 3. Thus, the light source 2 can be selected as appropriate depending on the type of concentration measuring sensor 5. For example if a concentration measuring sensor 5 having an infrared light receiving section is used as the concentration measuring sensor 5, then it is preferable to select an infrared light source as the light source 2. It is also possible to select a visible light source or an ultraviolet light source as the light source 2. In this embodiment, an infrared light source is selected because medical air is used as the sample gas and $CO_2$ is selected as the measurement target substance.

As further shown, light emitted from the light source 2 travels from the optical unit 3 as indicated by the optical path A and is introduced into the sample cell unit 4 arranged along the optical path of the light source 2. There are no particular limitations regarding the sample gas so long as the sample gas contains the measurement target substance. Any of various substances, such as $CO_2$ or $H_2O$, can be selected as the measurement target substance. In this example, the sample gas is introduced into the sample cell unit 4 through an inlet port provided on the sample cell unit 4. The reference numeral A1 indicates a path of the sample gas. In this embodiment, $CO_2$ is selected as the measurement target substance and medical air is selected as the sample gas containing the $CO_2$. Since $CO_2$ is selected as the measurement target substance, an infrared light source is used as the light source 2 because the concentration can be measured easily by utilizing the ability of $CO_2$ to absorb infrared light.

As further shown, the sample cell unit 4 includes a cylindrical main body section 20, an inlet port 21 for introducing sample gas into the main body section 20, and an outlet port 25 for discharging sample gas out from the main body section 20. An infrared passing window 6a can be provided on both ends of the main body section 20. There are no particular limitations on the material from which the sample cell unit 4 is made, and it is acceptable to use a cylindrical member made of stainless steel, aluminum, or vinyl chloride as the main body section. It is also acceptable to apply a metal plating of gold or other metal to an inside surface of the cylindrical member. Furthermore, there are no particular limitations on the material from which the infrared passing window is made, and such materials as calcium fluoride, sapphire, lithium fluoride, and barium fluoride can be used. In this embodiment, a stainless steel cylindrical member having a gold plating on an inside surface is used as the main body section 20 and the infrared passing windows 6a are made of calcium fluoride.

The concentration measuring sensor 5 is a sensor for measuring a concentration of the measurement target substance contained in the sample gas. The concentration measuring sensor 5 is arranged on an optical path of the light source 2 so that light emitted from the light source 2 passes through the measurement target substance inside the sample cell unit 4 before reaching the concentration measuring sensor 5.

A concentration measurement method (non-dispersive infrared analysis) for measuring a concentration of the measurement target substance using an infrared light source will now be explained. When infrared light emitted from the light source 2 passes through the sample gas, the measurement target substance contained in the sample gas absorbs infrared light having a wavelength that is unique to the measurement target substance. The concentration of the targeted component is measured by measuring the amount of infrared light absorbed at that wavelength. When calculating the concentration based on the amount of absorbed infrared light, the Lambert-Beer law is employed by using the general equation (1) shown below:

$$\log_{10}(I1/I0) = -\epsilon cl \quad (1)$$

with I0 representing an intensity of entering light, I1 representing an intensity of exiting light, $\epsilon$ representing a mole light absorption coefficient, c representing a sample concentration, and l representing a thickness of a light absorbing layer.

Thus, the infrared light emitted from the light source 2 passes through the sample cell portion and reaches the concentration measuring sensor 5. The concentration measuring sensor 5 incorporates a solid state infrared detector (pyrosensor) (not shown) and an optical filter (not shown) contrived to selectively pass a bandwidth of frequencies absorbed by $CO_2$ and a bandwidth of frequencies not absorbed by $CO_2$ (reference wavelength REF).

When the sample gas containing the $CO_2$ enters the sample cell section, infrared light of a wavelength unique to $CO_2$ is absorbed and the amount of infrared light incident on the concentration measuring sensor 5 at the corresponding wavelength decreases. Also, the amount of light incident on the reference detector (REF) does not change because a wavelength that is not absorbed has been selected. Thus, the concentration of $CO_2$ can be detected by calculating a difference between an output of the reference detector and an output of the concentration measuring sensor 5.

The introducing device 7 serves to discharge the sample gas from the sample cell unit 4, supply the discharged sample gas to the sensor unit 6 or the light source unit 3, and fill the inside of the sensor unit 6 or the light source unit 3 with an atmosphere of the sample gas. An embodiment in which the introducing device 7 supplies the sample gas to the sensor unit 6 will now be explained.

In the embodiment discussed above, a cover 41 is used to cover a connection portion disposed between the sample cell unit 4 and the sensor unit 6 as shown in FIG. 1 and sample gas discharged from the sample cell unit 4 is introduced to the inside of the cover. More specifically, the cover 41 serves as a discharging device and is arranged so as to cover an outer periphery of the main body section 20 of the sample cell unit 4. An inlet pipe 23 extending from the main body section 20 is connected to the cover 41. An outlet port 25 is also provided on the cover 41.

In another embodiment explained below, through holes (see FIGS. 3 and 4) are provided in a partitioning wall separating the sample cell unit 4 from the sensor unit 6 serve as the introducing device 7.

In a further embodiment explained later, a separate flow passage is provided to connect the sample cell unit 4 and the sensor unit 6, and a portion of the sensor unit 6 (side wall in FIG. 5) is configured to serve as an outlet for sample gas.

It should be noted that if an introducing device 7 is not provided, then the inside of the sensor unit 6 will be full of air. Consequently, air surrounding the apparatus flows in through the many gaps S as shown in FIG. 2. Thus, if the surrounding air contains the breath of a person, for example, and $CO_2$ is the measurement target substance, then $CO_2$ in the breath will flow inside to a vicinity of the concentration measuring sensor 5 and the apparatus will not be able to measure a $CO_2$ concentration in a stable and accurate manner. However, if through holes are provided in a partitioning wall separating the sample cell unit 4 from the sensor unit 6 as explained above, then the space inside the sensor unit 6 will be filled with sample gas entering through the through holes. Also, similarly to a case in which a cover 41 is provided as shown in FIGS. 1 and 2 of the first embodiment, the inside of the sensor unit 6—including the gaps S—is entirely filled with the sample gas. Consequently, even if a gas enters through a gap S, that gas will be the sample gas and the sample gas will not cause a measurement value to change even if it flows to a vicinity of the concentration measuring sensor 5. Thus, a stable and accurate measurement can be accomplished.

As further shown in FIG. 1, a light shuttering device 8 is configured to intermittently block infrared light emitted from an infrared light source is provided in the sensor unit 6 of a gas concentration measuring apparatus 1. The light shuttering device 8 serves to block the optical path such that infrared light emitted from the infrared light source reaches the concentration measuring sensor 5 inside the sensor unit 6 intermittently. Thus, a portion of the infrared light emitted from the infrared light source is absorbed by the measurement target substance inside the sample cell unit 4 and the amount of infrared light absorbed is detected by the concentration measuring sensor 5. However, if a pyroelectric infrared sensor or a condenser microphone is used as the concentration measuring sensor 5, then the detection of the amount of absorbed infrared light is dependent on the output of the detector at the moment when the infrared light reaches the detector. Therefore, the infrared light reaches the concentration measuring sensor 5 intermittently in order to continuously detect new data.

Also, while it is feasible to shine the infrared light emitted from the infrared light source in an intermittent manner, when the measurement target substance is $CO_2$, a Kanthal wire or other filament that emits a large amount of light can be used as the light source 2 because only a small amount of the measurement target substance is contained in the sample gas. When a light source 2 that emits a large amount of light is used, heat remains when the light source 2 transitions from a light emitting state to a non-light emitting state and there is a possibility that intermittent emission of the light will not be accomplished. Also, it is possible to obtain new data in a continuous fashion by allowing the infrared light source to shine continuously and providing a light shuttering device 8 to intermittently block the optical path before the infrared light reaches the concentration measuring sensor 5.

It should be further noted that there are no particular limitations on the light shuttering device 8. For example, a chopper 8b drivable with a motor 8a can be used, with reference numeral A2 indicating a rotational direction of the chopper 8b. As shown in FIG. 1, many gaps S exist around a perimeter of the chopper 8b drivable by the motor 8a, but all of these gaps S are covered by the cover 41 and the sample gas is introduced into the inside of the cover 41. Consequently, even if a gas enters through a gap S and flows to a vicinity of the concentration measuring sensor 5, that gas will be the sample gas and stable and accurate measurements can be accomplished without fluctuations of the measurement values occurring.

Although this embodiment presents an example in which a light shuttering device 8 is provided because a pyroelectric infrared sensor is used as the concentration measuring sensor 5, it is also possible to use, for example, a thermopile type infrared sensor or another type of sensor that can output an infrared light absorption amount directly as the concentration measuring sensor 5. In such a case, a light shuttering device 8 (chopper) is not necessary and, thus, there are no gaps along a perimeter of a chopper. However, even when such a sensor is used, the sensor is attached inside the sensor unit 6 with a mounting member that enables maintenance to be performed more easily. Consequently, it is possible for a gas to enter through a gap S existing due to the mounting member. In this embodiment, stable and accurate measurements can be accomplished regardless because all of the gaps S are covered with a cover 41 as explained previously.

With a gas concentration measuring apparatus 1 according to this embodiment, since a vicinity of the concentration measuring sensor 5 is filled with an atmosphere of the sample gas, a concentration of the measurement target substance in the sample gas can be measured stably and accurately even if an ambient atmosphere of a measuring environment fluctuates. Thus, a less expensive gas concentration measuring apparatus 1 can be provided because it is not necessary to prepare a separate purge gas, it is not necessary to protect the apparatus with a sealed case, and it is not necessary to design the apparatus so that gaps S are drastically reduced. Moreover, since the cover 41 used in this embodiment covers all of the gaps S around a periphery of the sample cell unit 4 and the inside of the cover 41 can be filled with the sample gas, the atmosphere of sample gas surrounding the concentration measuring sensor 5 can be prevented from changing even if a gas flows in through the gaps S.

Furthermore, it is preferable for the light source 2 to be an infrared light source. By using a light source 2 that emits infrared light, an amount of the emitted infrared light corresponding to the concentration of the measurement target substance contained in the sample gas will be absorbed when the measurement target substance is $CO_2$ or $H_2O$.

Also, a concentration of the measurement target substance can be measured by comparing a post-absorption infrared detection value to an infrared detection value of a measurement target gas having a known concentration. Furthermore, since a chopper 8b is provided as a light shuttering device 8 that operates to intermittently block the infrared light emitted from the infrared light source, instead of intermittently shining infrared light from the light source, the infrared light is shone continuously while the optical path of the infrared light is intermittently blocked. Consequently, it is possible to artificially treat the infrared light reaching the concentration measuring sensor 5 as intermittently emitted light.

A gas concentration measuring apparatus according to another embodiment is the same as in the first embodiment except that the measurement target substance is $H_2O$. Since the constituent features of the apparatus are the same as the gas concentration measuring apparatus 1 of the first embodiment shown in FIG. 1 and FIG. 2, the same reference numerals are used and explanations of constituent features are omitted. Thus, when the measurement target substance is $H_2O$, even if the humidity fluctuates due to geographic conditions of the measurement location, climatic changes, or the indoor ambient conditions, the sample gas can be introduced to a vicinity of the concentration measuring sensor 5 by the introducing device 7. Accordingly, a concentration of the measurement target substance in the sample gas can be measured stably and accurately without being affected by changes in the humidity of the air surrounding the gas concentration measuring apparatus.

Figure 3:
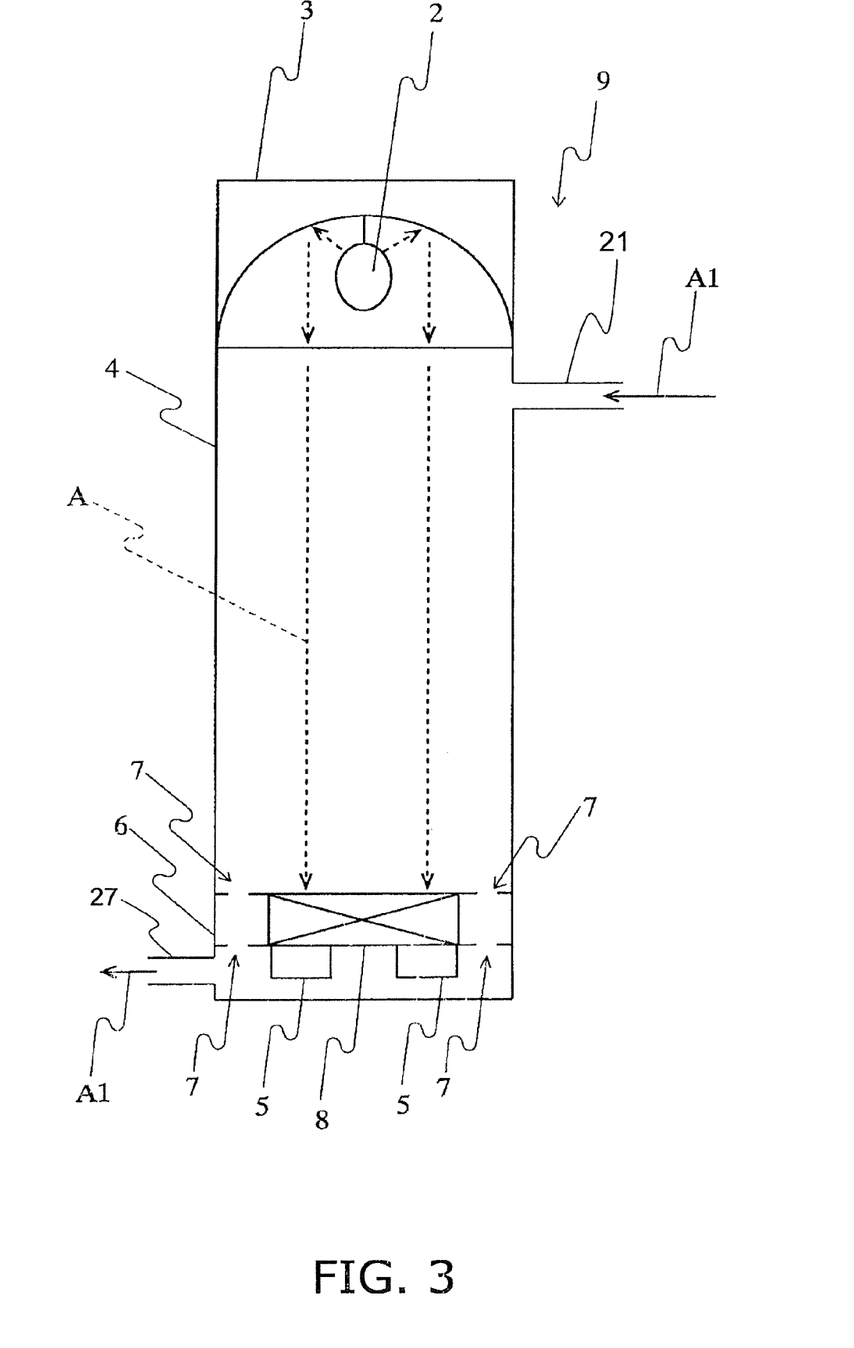
FIG. 3 is a schematic view illustrating a gas concentration measuring apparatus according to another exemplary embodiment.
Figure 4:
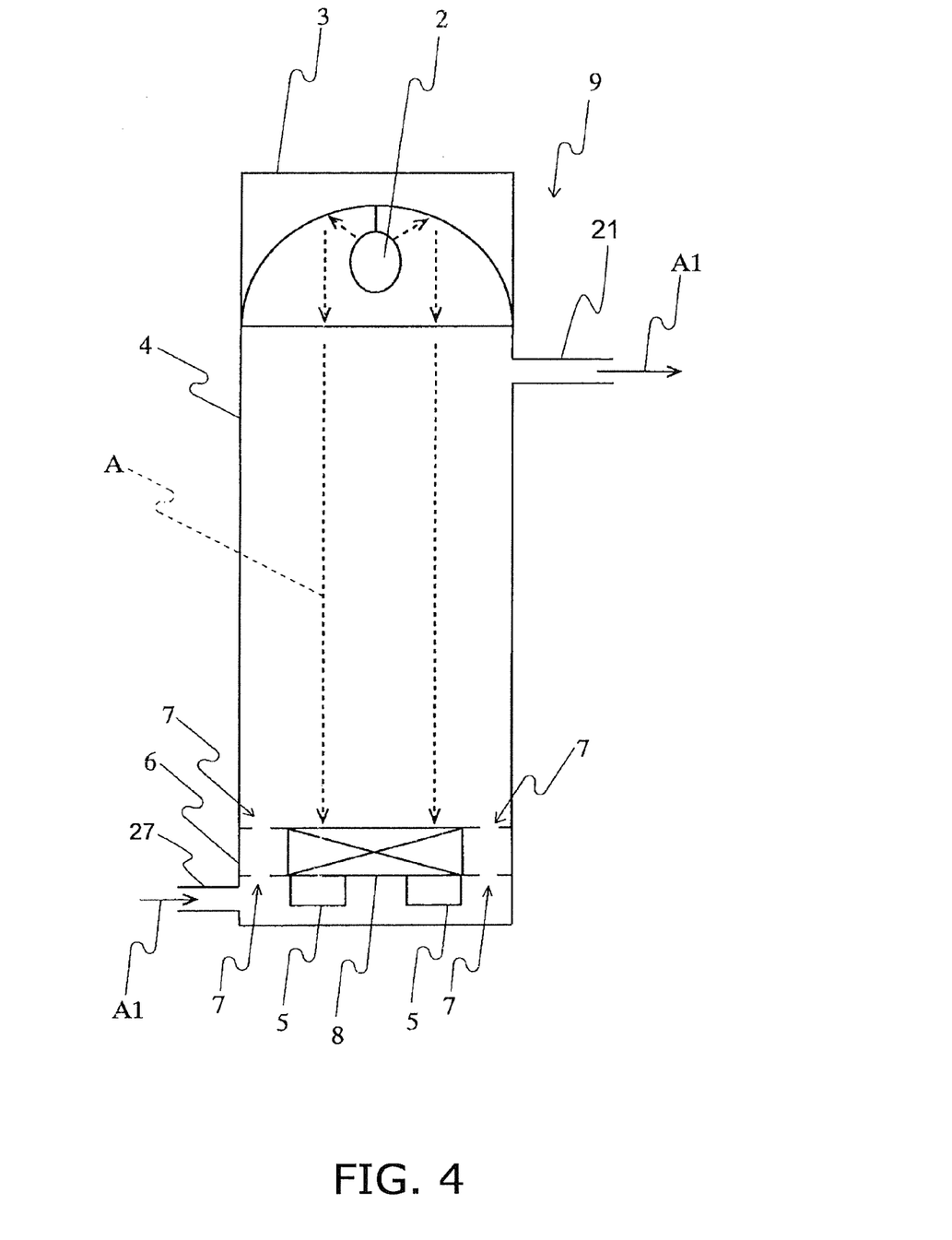
FIG. 4 is a schematic view further illustrating features of the gas concentration measuring apparatus shown in FIG. 3.

A gas concentration measuring apparatus 9 according to a further embodiment is the same as in the first embodiment except that through holes serving as an introducing device 7 are provided in a partitioning wall separating the sample cell unit 4 and the sensor unit 6 from each other as shown in FIG. 3 and FIG. 4. Therefore, the same reference numerals are used for the same parts and explanations are omitted. As shown in FIG. 3, the sample gas is introduced through an inlet port 21 provided on the sample cell unit and discharged through an outlet port 27 provided on the sensor unit 6. When the sample gas is medical air or another gas that is not particularly contaminated, the inlet port 21 shown in FIG. 3 can be used as an outlet port and the outlet port 27 shown in FIG. 3 can be used as an inlet port as shown in FIG. 4 because there is no risk that the concentration measuring sensor 5 inside the sensor unit 6 or the surrounding vicinity will become contaminated.

Figure 5:
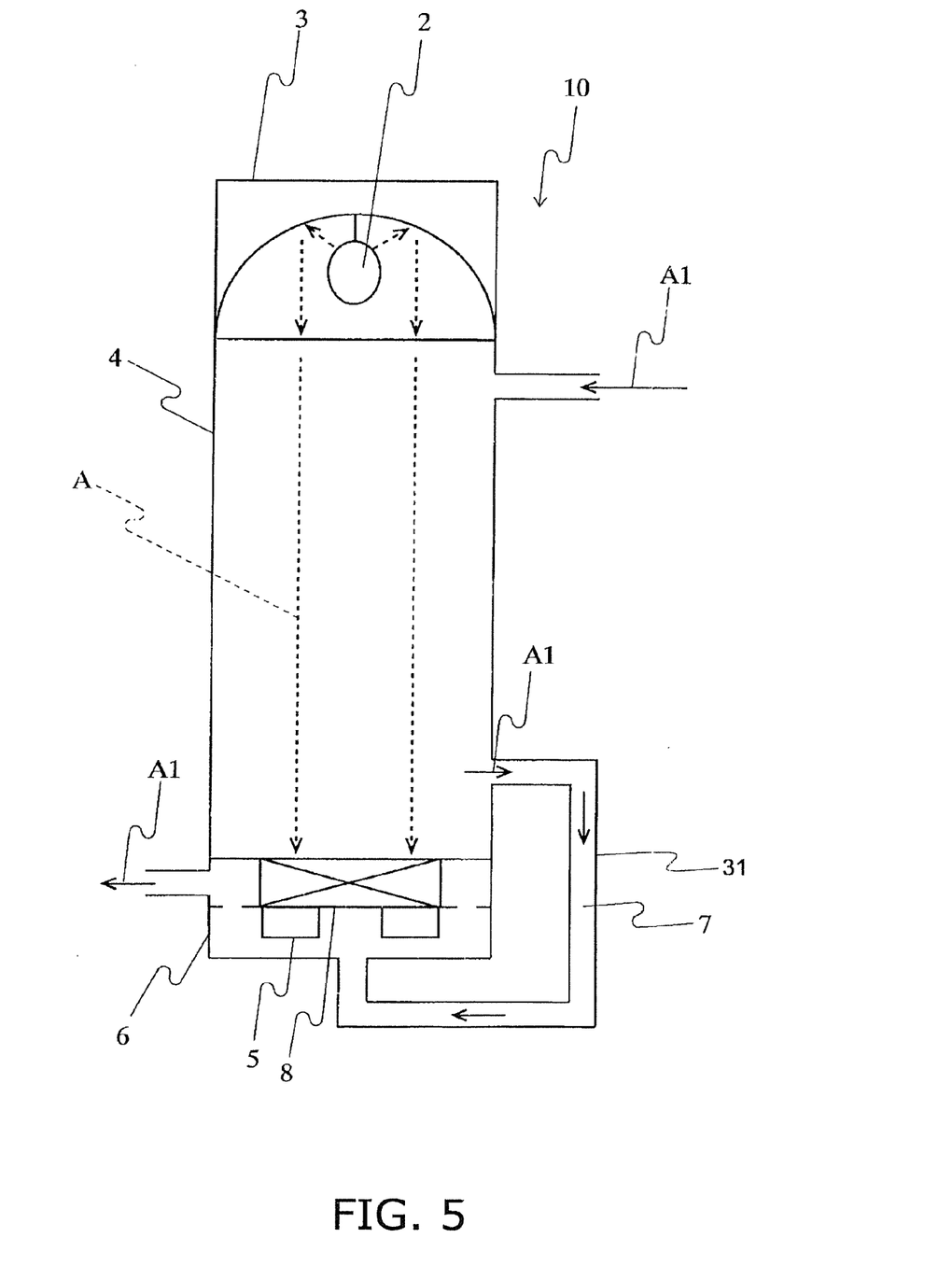
FIG. 5 is a schematic view illustrating a gas concentration measuring apparatus according to a further exemplary embodiment.

A gas concentration measuring apparatus 10 according to yet another embodiment is the same as in the first embodiment except that, as shown in FIG. 5, a flow passage 31 connecting the sample cell unit 4 and the sensor unit 6 together is provided as an introducing device 7 and a sample gas outlet port 27 is provided on the sensor unit 6. Therefore, the same reference numerals are used for the same parts and explanations are omitted. Although in FIG. 5 the flow passage 31 is connected between a lower portion of a side wall of the sample cell unit 4 and a bottom portion of the sensor unit 6, there are no particular limitations on the location of the flow passage.

Figure 6:
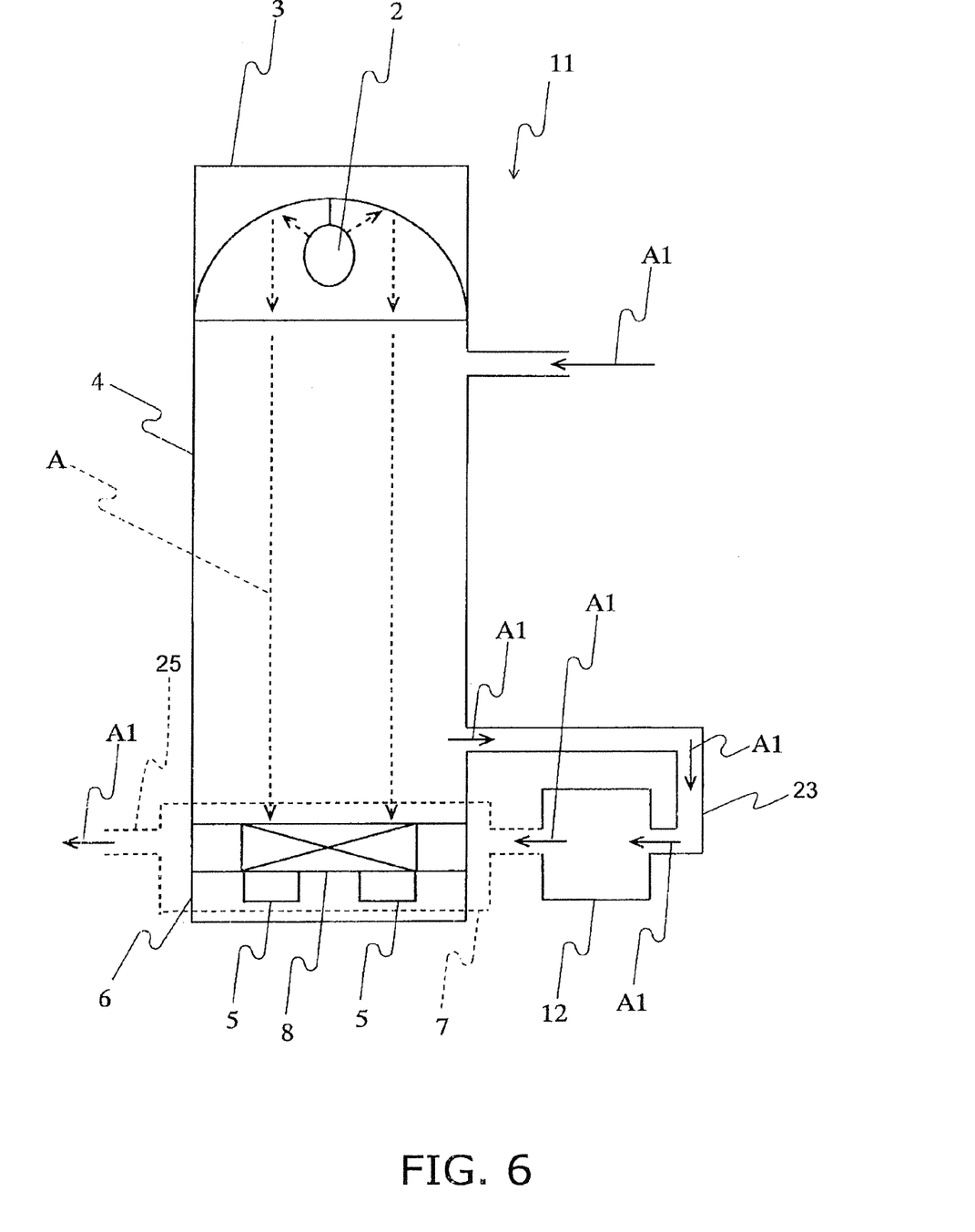
FIG. 6 is a schematic view illustrating a gas concentration measuring apparatus according to another exemplary embodiment.

A gas concentration measuring apparatus 11 according to still another embodiment is the same as in the first embodiment except that a scrubber 12 is provided in the introducing device 7 as shown in FIG. 6. Therefore, the same reference numerals are used for the same parts and explanations are omitted.

The scrubber 12 is provided to prevent contamination in a vicinity of the concentration measuring sensor 5 and prevent malfunctions caused by contamination when the sample gas is an exhaust gas containing particles or other contaminants. Also, there are no particular limitations on the scrubber 12. For example, a scrubber filled with activated carbon on the inside can be used in this embodiment.

With a gas concentration measuring apparatus according to the embodiments explained above, since a vicinity of the concentration measuring sensor is filled with an atmosphere of the sample gas, it is possible to provide a gas concentration measuring apparatus that can measure a concentration of a measurement target substance in the sample gas stably and accurately regardless of fluctuations in an ambient atmosphere of the measuring environment. Moreover, a less expensive gas concentration measuring apparatus can be provided because it is not necessary to prepare a separate purge gas, it is not necessary to protect the apparatus with a sealed case, and it is not necessary to design the apparatus such that gaps are drastically reduced. Also, even if the measurement target gas is a contaminated gas contaminated with dust or other particles, the particles can be removed from the gas and the concentration measuring sensor can be prevented from becoming contaminated and malfunctioning due to the contamination.

Figure 7:
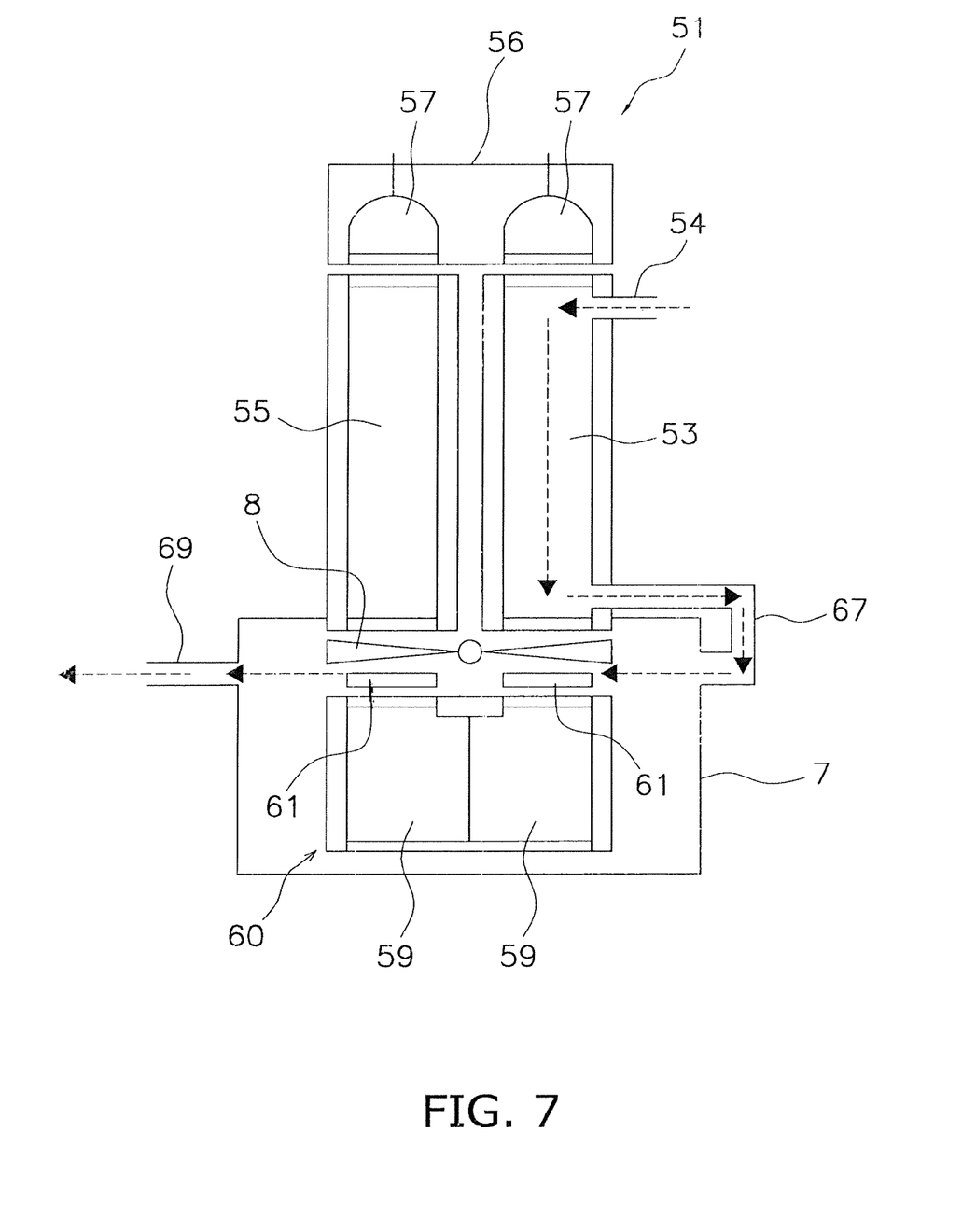
FIG. 7 is a schematic view illustrating a gas concentration measuring apparatus according to a further exemplary embodiment.

In a gas concentration measuring apparatus 51 according to any of the embodiments explained below, a sample cell unit 53 and a comparison cell unit 55 are arranged adjacently as shown in FIG. 7. Also, a pair of light sources 57, a pair of concentration measuring sensors 59 (examples including a condenser microphone or other pneumatic detector), and a pair of optical filters 61 are provided, with the members of each pair corresponding to one or the other of the cell units 53 and 55. A chopper that operates as a light shuttering device 8 is provided between the pair of optical filters 61 and the sample cell unit 53 and comparison cell unit 55. An inlet port 54 through which a sample gas is introduced is provided on the sample cell unit 53.

In this embodiment, a concentration measuring sensor 59, an optical filter 61, and a light shuttering device 8 constitute a sensor unit 60 as explained previously. The sensor unit 60 is covered with a sealed case serving as an introducing device 7. An inlet pipe 67 extending from the sample cell unit 53 is connected to the sealed case. An outlet port 69 through which sample gas is discharged is provided on the sealed case.

Since the inside of the sealed case can be filled with the sample gas in this embodiment, the ambient atmosphere of sample gas surrounding the concentration measuring sensor can be prevented from undergoing fluctuations. As a result, a concentration of a measurement target substance contained in a sample gas can be measured more stably and accurately.

Figure 8:
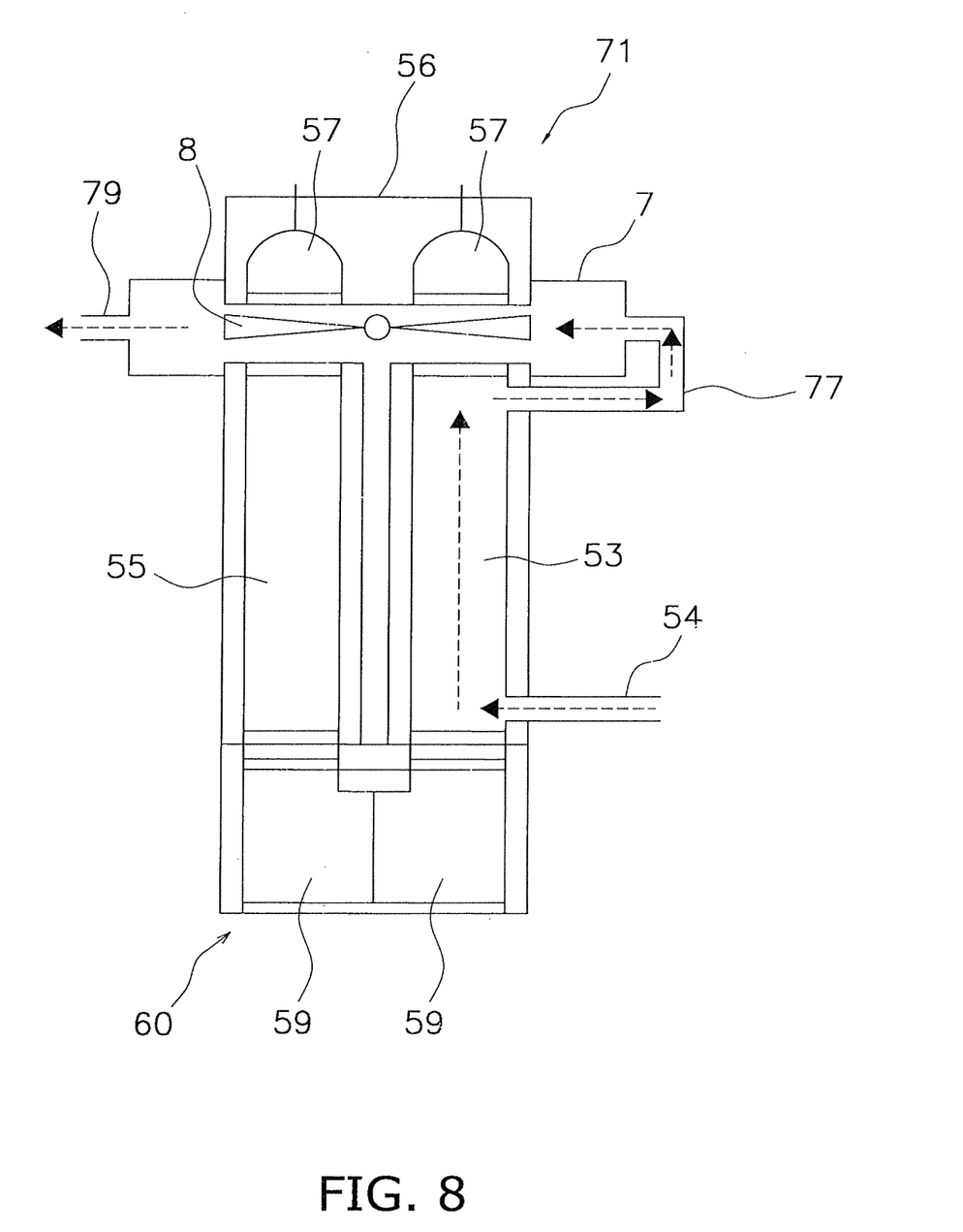
FIG. 8 is a schematic view illustrating a gas concentration measuring apparatus according to yet another exemplary embodiment.

Another embodiment in which the introducing device 7 supplies a sample gas to the light source unit 3 will now be explained. Since the structure of the gas concentration measuring apparatus 71 is basically the same as the sixth embodiment, explanations thereof are omitted.

As shown in FIG. 8, the optical shuttering device 8 is arranged on the side where the light source 57 is located and is a portion of the light source unit 56. The gas concentration measuring apparatus 71 has a cover serving as an introducing device 7 that covers a space in the light source unit 3 where the light shuttering device 8 is arranged. The sample gas is introduced to the cover after being discharged from the sample cell unit 53. An inlet pipe 77 extending from the sample cell unit 53 is connected to the cover. An outlet port 79 is also provided on the cover. As a result, the inside of the light source unit 56 is filled with the sample gas. Thus, stable and accurate measurements can be obtained.

It is also acceptable to cover the entire light source unit with a cover serving as an introducing device. It is further acceptable to provide a scrubber in the inlet pipe, and to provide through holes in a partitioning wall on the light source side of the sample cell as an introducing device.

As can be appreciated form the above, the previously explained embodiments have a light shuttering device. However, it is acceptable provide an introducing device in a gas concentration measuring apparatus that does not have a light shuttering device. In such a case, the same effects as explained previously can be obtained. Also, the infrared light emitted from the infrared light source can be shone intermittently.

A gas concentration measuring apparatus according to the previously explained embodiments will now be explained more concretely using a working example. The concentration of $CO_2$ in a sample gas of N2 gas was measured using the gas concentration measuring apparatus 1 shown in FIG. 1 and FIG. 2. The measurements where conducted continuously for 18 hours starting at 14:00 on 3 Aug. 2010. A summary of the gas concentration measuring apparatus is as follows:

Light source: infrared light source (Kanthal wire, approximately 7 W);

Sample gas: $N_2$ (flow rate: 1 L/min);

Measurement target substance: $CO_2$;

Concentration measuring sensor: pyroelectric infrared detector (pyrosensor);

Light shuttering device: chopper (rotation frequency: 5 Hz);

Introducing device: plastic cover;

Installation location of gas concentration measuring apparatus: a laboratory inside Horiba, Ltd.

First Working Example

Figure 9:
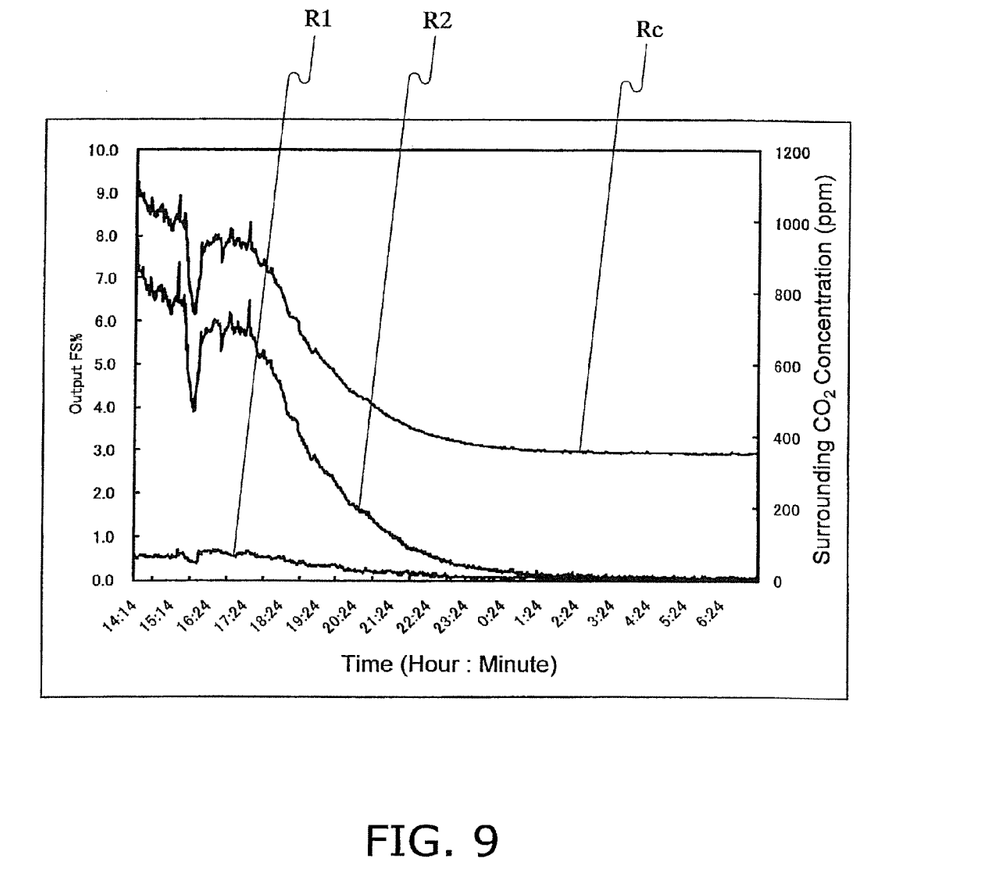
FIG. 9 is a graph showing results of a $CO_2$ concentration measurement test performed using a gas concentration measuring apparatus according to a first working example and a gas concentration measuring apparatus according to a first comparative example.

Changes in a $CO_2$ concentration over time were measured using the aforementioned gas concentration measuring apparatus. Results are shown in FIG. 9. The reference symbol Rc in Table 1 indicates an ambient $CO_2$ concentration (ppm), and the reference symbol R1 indicates a $CO_2$ concentration measurement result (FS % (full scale %)) of the first working example.

First Comparative Example

Changes in a $CO_2$ concentration over time were measured using the aforementioned gas concentration measuring apparatus not provided with an introducing means. Results are shown in FIG. 9. The reference symbol R2 indicates a $CO_2$ concentration measurement result (FS %) of the comparative example. As shown in FIG. 9, the $CO_2$ concentration values detected with the gas concentration measuring apparatus of the first comparative example, which is not provided with an introducing device, changed in response to changes of the ambient $CO_2$ concentration while $CO_2$ concentration values detected with the gas concentration measuring apparatus of the first embodiment, which is provided with an introducing device, did not change even if the ambient $CO_2$ concentration changed.

Although different embodiments of the present invention are explained herein, the present invention is not limited to these embodiments and various modifications can be made without departing from the scope of the invention. In particular, the embodiments and variations presented in this specification can be combined in any way as necessary. For example, it is acceptable to use the introducing device according to the embodiments shown in FIGS. 7 and 8 in a gas concentration measuring apparatus having the basic structure presented in the embodiments shown in FIGS. 1-6. It is also acceptable to use an introducing device according to any one of the embodiments shown in FIGS. 1-6 in a gas concentration measuring apparatus having the basic structure presented in the embodiments shown in FIGS. 7 and 8. Although in the previously explained embodiments an introducing device is provided only on the light source side or the sensor side, it is acceptable to provide an introducing device on both the light source side and the sensor side.

With the previously explained embodiments, since a vicinity of the concentration measuring sensor is filled with an atmosphere of the sample gas, it is possible to provide a gas concentration measuring apparatus that can measure a concentration of a measurement target substance in the sample gas stably and accurately regardless of fluctuations in an ambient atmosphere of the measuring environment. Moreover, a less expensive gas concentration measuring apparatus can be provided because it is not necessary to prepare a separate purge gas, it is not necessary to protect the apparatus with a sealed case, and it is not necessary to design the apparatus such that gaps are drastically reduced.

What is claimed is:

1. A gas concentration measuring apparatus for measuring a concentration of a measurement target substance contained in a sample gas, the gas concentration measuring apparatus comprising:
    a light source unit having a light source;
    a sample cell unit that is arranged on an optical path of the light source and configured to receive a sample gas;
    a sensor unit that is arranged on an optical path of the light source and includes a concentration measuring sensor configured to receive light from the light source after the light has passed through the sample cell unit and measure a concentration of the measurement target substance; and
    an introducing device configured to discharge the sample gas from the sample cell unit, supply the discharged sample gas to a vicinity of the sensor unit or the light source unit, and fill an inside of the sensor unit or the light source unit with an atmosphere of the sample gas;
    the introducing device including a cover that covers a gap formed at a boundary of the sample cell unit, a boundary of the sensor unit, or a boundary of the light source unit from an outer periphery of the sample cell unit, the sensor unit, or the light source unit, and the introducing device further including a flow passage that connects the sample cell unit to the cover.

2. A gas concentration measuring apparatus for measuring a concentration of a measurement target substance contained in a sample gas, the gas concentration measuring apparatus comprising:
    a light source unit having a light source;
    a sample cell unit that is arranged on an optical path of the light source and configured to receive a sample gas;
    a sensor unit that is arranged on an optical path of the light source and includes a concentration measuring sensor configured to receive light from the light source after the light has passed through the sample cell unit and measure a concentration of the measurement target substance;
    an introducing device configured to discharge the sample gas from the sample cell unit, supply the discharged sample gas to a vicinity of the sensor unit or the light source unit, and fill an inside of the sensor unit or the light source unit with an atmosphere of the sample gas, the introducing device including a cover that covers a gap formed at a boundary of the sample cell unit, a boundary of the sensor unit, or a boundary of the light source unit from an outer periphery of the sample cell unit, the sensor unit, or the light source unit; and
    a light shuttering mechanism that is arranged near the concentration measuring sensor or the light source and configured to intermittently block infrared light emitted from the light source.

3. The gas concentration measuring apparatus according to claim 2, wherein
    the light shuttering mechanism includes a chopper.

4. The gas concentration measuring apparatus according to claim 2, wherein
    the introducing device is provided near the light shuttering mechanism.

5. The gas concentration measuring apparatus according to claim 3, wherein
    the introducing device is provided near the light shuttering mechanism.

6. The gas concentration measuring apparatus according to claim 1, wherein
the introducing device further comprises a scrubber.
7. The gas concentration measuring apparatus according to claim 1, wherein
the cover covers the entire sensor unit or the entire light source unit.
8. The gas concentration measuring apparatus according to claim 7, wherein
the introducing device further includes a scrubber.
9. The gas concentration measuring apparatus according to claim 1, wherein
the measurement target substance contained in the sample gas is carbon dioxide or water.
10. A gas concentration measuring apparatus for measuring a concentration of a measurement target substance contained in a sample gas, the gas concentration measuring apparatus comprising:
a light source unit defining a light source space having a light source disposed therein;
a sample cell unit that is arranged on an optical path of the light source and configured to receive a sample gas;
a sensor unit that is arranged on an optical path of the light source and defines a sensor unit space including a concentration measuring sensor disposed therein, the concentration measuring sensor being configured to receive light from the light source after the light has passed through the sample cell unit and measure a concentration of the measurement target substance; and
an introducing device configured to discharge the sample gas from the sample cell unit, supply the discharged sample gas to a vicinity of the sensor unit or the light source unit, and fill an inside of the sensor unit or the light source unit with an atmosphere of the sample gas;
the introducing device including a partitioning wall in which a through hole is formed, the partitioning wall separating the sample cell unit from the sensor unit or the light source unit such that the through hole provides communication between the sample cell unit and the sensor unit or the light source unit; and
the light source space defining an inlet or an outlet of a flow passage of the sample gas, or the sensor unit space defining the inlet or the outlet of the flow passage of the sample gas.
11. A gas concentration measuring apparatus for measuring a concentration of a measurement target substance contained in a sample gas, the gas concentration measuring apparatus comprising:
a light source unit having a light source;
a sample cell unit that is arranged on an optical path of the light source and configured to receive a sample gas;
a sensor unit that is arranged on an optical path of the light source and includes a concentration measuring sensor configured to receive light from the light source after the light has passed through the sample cell unit and measure a concentration of the measurement target substance;
an introducing device configured to discharge the sample gas from the sample cell unit, supply the discharged sample gas to a vicinity of the sensor unit or the light source unit, and fill an inside of the sensor unit or the light source unit with an atmosphere of the sample gas,
the introducing device including a partitioning wall in which a through hole is formed, the partitioning wall separating the sample cell unit from the sensor unit or the light source unit such that the through hole provides communication between the sample cell unit and the sensor unit or the light source unit; and
a light shuttering mechanism that is arranged near the concentration measuring sensor or the light source and configured to intermittently block infrared light emitted from the light source.
12. The gas concentration measuring apparatus according to claim 10, wherein
the measurement target substance contained in the sample gas is carbon dioxide or water.
13. A gas concentration measuring apparatus for measuring a concentration of a measurement target substance contained in a sample gas, the gas concentration measuring apparatus comprising:
a light source unit including a light source;
a sample cell unit that is arranged on an optical path of the light source and configured to receive a sample gas;
a sensor unit that is arranged on an optical path of the light source and includes a concentration measuring sensor configured to receive light from the light source after the light has passed through the sample cell unit and measure a concentration of the measurement target substance;
a light shuttering mechanism that is arranged near the concentration measuring sensor or the light source and configured to intermittently block infrared light emitted from the light source; and
a gas supply passage configured to supply a sample gas to a space in which the light shuttering mechanism is arranged.
14. The gas concentration measuring apparatus according to claim 13, wherein
the light shuttering mechanism includes a chopper.
15. The gas concentration measuring apparatus according to claim 13, wherein
the gas supply passage includes a cover that covers a gap formed at a boundary of the sample cell unit, a boundary of the sensor unit, or a boundary of the light source unit from an outer periphery of the sample cell unit, the sensor unit, or the light source unit.
16. The gas concentration measuring apparatus according to claim 1, wherein
the introducing device includes a partitioning wall separating the sample cell unit from the sensor unit or the light source unit such that the flow passage is configured as a through hole that provides communication between the sample cell unit and the sensor unit or the light source unit.
17. The gas concentration measuring apparatus according to claim 10, wherein the introducing device has one of the following configurations:
the light source space defines the inlet of the flow passage and the sensor unit space defines the outlet of the flow passage of the sample gas; and
the sensor unit space defines the inlet of the flow passage and the light source space defines the outlet of the flow passage of the sample gas.

* * * * *